United States Patent
Vuiblet et al.

(10) Patent No.: US 9,810,625 B2
(45) Date of Patent: Nov. 7, 2017

(54) METHOD FOR DETECTING AND QUANTIFYING FIBROSIS

(71) Applicant: UNIVERSITE DE REIMS CHAMPAGNE-ARDENNE, Reims (FR)

(72) Inventors: Vincent Vuiblet, Chenay (FR); Olivier Piot, Cormontreuil (FR); Philippe Rieu, Merfy (FR); Michael Fere, Reims (FR); Cyril Gobinet, Athies-Sous-Laon (FR)

(73) Assignee: UNIVERSITE DE REIMS CHAMPAGNE-ARDENNE, Reims (FR)

( * ) Notice: Subject to any disclaimer, the term of this patent is extended or adjusted under 35 U.S.C. 154(b) by 0 days.

(21) Appl. No.: 15/329,011

(22) PCT Filed: Jul. 2, 2015

(86) PCT No.: PCT/FR2015/051826
§ 371 (c)(1),
(2) Date: Jan. 25, 2017

(87) PCT Pub. No.: WO2016/016531
PCT Pub. Date: Feb. 4, 2016

(65) Prior Publication Data
US 2017/0212041 A1    Jul. 27, 2017

(30) Foreign Application Priority Data
Jul. 29, 2014   (FR) ...................................... 14 57323

(51) Int. Cl.
*G01N 21/35* (2014.01)
*G01N 21/3563* (2014.01)
(Continued)

(52) U.S. Cl.
CPC ..... *G01N 21/3563* (2013.01); *G01N 33/5091* (2013.01); *G01N 2021/3196* (2013.01);
(Continued)

(58) Field of Classification Search
CPC ................. G01N 21/359; G01N 21/35; G01N 2291/02475; G01N 33/5005; A61B 5/0075; G01J 3/28
See application file for complete search history.

(56) References Cited

U.S. PATENT DOCUMENTS

| | | | | |
|---|---|---|---|---|
| 6,146,897 A | * | 11/2000 | Cohenford | ................ G01J 3/28 250/338.1 |
| 2004/0019269 A1 | * | 1/2004 | Schaefer | ................ G01N 25/72 600/407 |

(Continued)

FOREIGN PATENT DOCUMENTS

| | | | | |
|---|---|---|---|---|
| EP | 2302359 A1 | * | 3/2011 | ......... G01N 33/6893 |
| WO | 02 46722 A2 | | 6/2002 | |

OTHER PUBLICATIONS

Jayakrupakar Nallala et al: "Infrared spectral histopathology for cancer diagnosis: a novel approach for automated pattern recorgnition of colon adenocarcinoma", The Analyst, vol. 139, No. 16, Jun. 12, 2014, pp. 4005-4015; abstract, p. 4006, right col, I. 2 to p. 4007, left col., paragraph 1.

(Continued)

*Primary Examiner* — Marcus Taningco
(74) *Attorney, Agent, or Firm* — Andrew W. Chu; Craft Chu PLLC

(57) ABSTRACT

A method for detecting and quantifying fibrosis, which involves at least; positioning a non-colored fixed tissue sample on a support; carrying out infrared acquisition, by scanning, of points of the sample; converting the infrared spectrum produced by each acquired point into at least one spectral image; carrying out a digital processing operation (Continued)

on the spectral image by distinguishing between at least physiological collagen and pathological collagen from fibrosis, attributing, to each point, a spectral class defined by an algorithm classifying the spectra according to the spectral similarities % thereof, then attributing a status to each class by statistically comparing with a digital model of spectra; quantifying the relative surface area occupied by the points of each status; and recording the result.

9 Claims, 1 Drawing Sheet

(51) Int. Cl.
G01N 33/50 (2006.01)
G01N 21/31 (2006.01)
(52) U.S. Cl.
CPC . G01N 2021/3595 (2013.01); G01N 2201/10 (2013.01); G01N 2201/129 (2013.01)

(56) References Cited

U.S. PATENT DOCUMENTS

2013/0317369 A1* 11/2013 Bryant-Greenwood A61B 5/0059
600/476
2015/0051233 A1* 2/2015 Tweardy ............... C07C 317/28
514/274

OTHER PUBLICATIONS

Kwak Jin Tae et al: "Multimodal microscopy for automated histologic analysis of prostate cancer", BMC Cancer, Biomed Central, London, GB, vol. 11, No. 1, Feb. 9, 2011, p. 62.

Nallala Jayakrupakar et al: "Infrared spectral imaging as a novel approach for histopathological recognition in colon cancer diagnosis", Journal of Biomedical Optics, SPIE-International Society for Optical Engineering, US, vol. 17, No. 11, Nov. 1, 2012, p. 116013.

* cited by examiner

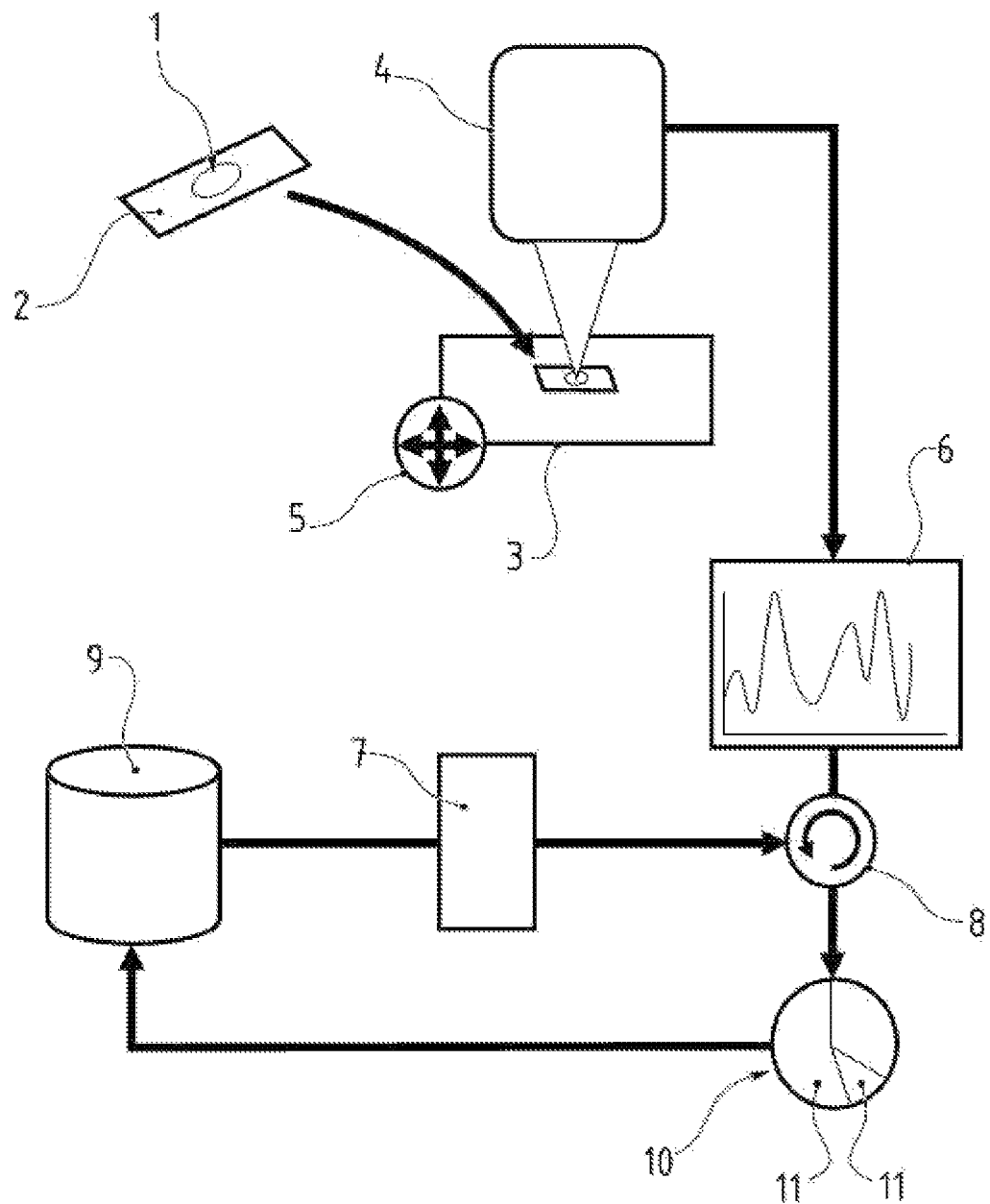

METHOD FOR DETECTING AND QUANTIFYING FIBROSIS

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention enters the medical field, for diagnosing and following up the time-dependent change in tissue fibrosis.

For this purpose, the invention particularly relates to a system for detecting and quantifying tissue fibrosis.

2. Description of Related Art Including Information Disclosed Under 37 CFR 1.97 and 37 CFR 1.98.

Tissue fibrosis refers to the accumulation of extracellular matrix within the connective tissue. Fibrosis occurs following an inflammation or a lesion of said tissue. The latter will not naturally and properly regenerate.

Fibrosis is a process for accumulating collagen which is synthesized by cells in the connective tissue. Collagen is a protein family physiologically present in the body notably for giving the tissue its mechanical resistance properties upon stretching. However, within the parenchyma of an organ, the excessive accumulation of collagen, therefore of resulting connective tissue of the fibrosis, causes a gradual, often inexorable, of the function of the organ.

Therefore, there exist several types of fibroses altering the function of the organs and causing diverse pathologies.

One refers to lung fibrosis in order to designate alteration of the lung connective tissue, the alveola of which are then found clasped and smothered by collagen fibers.

One refers to liver fibrosis for a fibrous connective tissue developing where liver cells have been destroyed. When liver fibrosis extends, it may result in the development of cirrhosis.

One also refers to kidney fibrosis which corresponds to an excessive accumulation of extracellular matrix in the renal parenchyma.

In other words, there exists a close correlation between the degree of fibrosis of an organ and its function. Generally, the more excessive is the accumulation of collagen in connective tissues, the larger is the loss of the function of the organ.

Accordingly, specifically quantifying tissue fibrosis is necessary in order to define a vital or functional prognosis and for following up the time-dependent change in an existing fibrosis.

In a known way, quantification of the fibrosis of a tissue is achieved on colored slides. An anatomopathologist will establish a score depending on the relative surface area occupied by fibrosis within the biopsy.

By "biopsy" is meant the fact of sampling a quite small portion of an organ or of a tissue in order to carry out medical examinations. This analysis technique on colored slides has the disadvantage of being subjective since it is not achieved by the human eye. This means for quantifying fibrosis therefore has poor intra-user and inter-user reproducibility, and therefore this quantification is not very representative and lacks reliability.

In order to overcome this limitation of the subjective quantification on colored slides, producing a semi-automated colorimetric quantification is also known. This technique consists in a semi-automated and computerized analysis based on automatic segmentation of the colors present on the slides colored with Masson Trichromium. The technique consists of setting tissue biopsies, dehydrating them, and then including them in paraffin. Sections of paraffin of four to ten micrometers ($\mu$m) are spread out on supports of the slide type, notably compatible with Fourier Transform Infrared Spectroscopy ("FTIRS") and then colored with Masson Trichromium. Masson Trichromium colors in green the collagen fibers.

After staining with Masson Trichromium, the slides are scanned and then, from the obtained images, an operator selects the confusion areas appearing in green, i.e. the areas where collagen is physiologically present. The image after selection then undergoes a computerized processing based on an algorithm based on the segmentation of colors, identifying over three channels the red, green and blue colors, the green corresponding to the connective tissue with an excess of collagen and therefore to the fibrosis.

However, this semi-automated colorimetric quantification has the drawback of requiring a manual step for removing the confusion areas, introducing a share of subjectivity and an additional processing time.

Further, to this day, this technique has only been validated at renal tissue. Moreover, this technique systematically over-evaluates renal fibrosis. Indeed, the renal tubular basal membranes are made up of collagen, therefore colored in green and considered as fibrosis. This drawback is all the more important since the tubes are jointed and therefore the interstitial fibrosis is minimal. Thus, on a biopsy without any fibrosis, a 15 to 20% quantification of fibrosis is obtained, displaying an over-estimation of said quantification.

The semi-automatic colorimetric quantification does not allow differentiation of the different types of collagens within a same tissue, since it is based on a green coloration coloring all the collagens. Although reproducible for renal tissue fibrosis, the semi-automated colorimetric quantification therefore lacks representativity.

An equivalent technique uses Raman spectroscopy. It is also known for quantifying fibrosis, notably at the hepatic level, the Second-Harmonic Generation technique (SHG) which allows achieving a semi-automated quantification of collagen of type I present in the tissues. The SHG technique is based on the specific emission of collagen of type I after excitation by a two-photon microscope. After setting the tissue biopsies, dehydrating and inclusion in paraffin, sections from 4 to 6 μm were made and then spread out on supports compatible with FTIR, without any coloration. The tissue biopsies present on the slides are segmented into several fragments and then concatenated by the system. After excitation, the collagen of type I will emit an SHG signal. On each section, the SHG signal is detected. The tissue SHG signal is quantified via a semi-automated digital processing operation. An operator will have to define for each image or group of images the noise and positivity threshold values of the SHG signal. A quantification algorithm thus processes each image. The algorithm will calculate as a result the relative surface area occupied by the SHG signal, specific to the collagen of type I, for each biopsy according to the thresholds defined by the operator. The result of this is that this technique has as a drawback an intervention of the user who has to subjectively determine a positivity threshold of the SHG signal.

Further, the SHG imaging has been described exclusively for liver and lung fibrosis.

Further, the SHG technique has as another drawback of not distinguishing the fibrosis of the histological structures including collagen of type I physiologically like normal connective tissues. This SHG technique then allows detection of the whole of the collagen of type I present in the tissue.

The object of the present invention is to overcome the drawbacks of the methods mentioned earlier, by proposing a system for detecting fibrosis which is capable of quantifying and of following the time-dependent change of tissue fibrosis in an automatic reproducible and objective way by doing without the intervention of the operator. This system allows distinction of the different collagen histological structures, i.e. the connective tissue involved in the pathological tissue fibrosis of the connective tissue physiologically present.

BRIEF SUMMARY OF THE INVENTION

Such a system first of all includes a method for detecting and quantifying fibrosis in which at least:
  a fixed non-colored tissue sample is positioned on a support;
  infrared acquisition by sweeping points of said sample is carried out;
  the infrared spectrum produced by each acquired point is converted into at least one spectral image;
  a digital processing operation is carried out on said spectral image by discrimination between at least physiological collagen and pathological collagen from the fibrosis by assigning to each point a spectral class defined by an algorithm classifying the spectra according to their spectral similarities;
  a state is then assigned to each class by statistical comparison with a numerical model of spectra;
  the relative surface area occupied by the points of each state is quantified and the result is recorded.

According to other additional, non-limiting features:
  said infrared acquisition is carried out by Fourier transform infrared spectroscopy.
  said processing comprises a preliminary pre-processing step, consisting in removing from the spectrum background noise from the support and from the detector and in the neutralization of the interferences of the paraffin.
  said classes are four in number, the state of which are designated as: normal, fibrosis, non-fibrous collagen, inflammation.
  said discrimination is carried out by comparing the value of the spectrum of each point with ranges of spectrum values of said model,
  the points of a small class are statistically quantified as a surface percentage of the total surface area of said sample.
  said result is combined with said model before repeating said method with another sample.

Further, said system also comprises a device for detecting and quantifying fibrosis, allowing the application of the method according to the invention. Such a device comprises at least:
  means for receiving a support of a tissue sample;
  means for acquiring by Fourier transform infrared spectroscopy positioned facing said receiving means, said acquisition means converting the infrared spectrum produced by each acquired point into a spectral image;
  digital processing means of said spectral image by discrimination between at least physiological collagen and pathological collagen by assigning to each point, a spectral class by statistical comparison with a numerical model of spectra, with which said processing means are provided, said processing means quantifying the points having a similar spectral class;
  digital recording means for the result of said processing means.

According to other additional, non-limiting features:
  said receiving means are motor-driven and said device comprises means for controlling the displacements of said receiving means, so as to perform a relative sweep of said support by said infrared acquisition means.

Other features and advantages of the invention will become apparent from the detailed description which follows of non-limiting embodiments of the invention, with reference to the appended FIGURE, schematically illustrating the architecture of the system for detecting and quantifying fibrosis of a sample.

BRIEF DESCRIPTION OF THE SEVERAL VIEWS OF THE DRAWINGS

The FIGURE shows a schematic view of the present invention relating to a system for detecting and quantifying fibrosis within a sample.

DETAILED DESCRIPTION OF THE INVENTION

Said sample 1 consists in a tissue sample. First of all, the sample 1 is set so that it retains a condition as close as possible to the condition in vivo. The setting of the sample may be chemical, for example with formol, AFA, or Bouin's Liquid, or may be physical, for example by freezing or freeze-drying. The set sample 1 is then dehydrated. The dehydration is carried out by means known to one skilled in the art, for example by means of a robot or for example in increasing alcohol baths and by using intermediate organic solvents such as xylene and toluene.

Said sample 1 is included in paraffin or in resin in order to obtain a hard block. The inclusion consists in an impregnation of the sample in super-cooled paraffin, and then there is cold polymerization. After inclusion of the sample, a section of the included sample is produced by means of known microtomy techniques. Such a section of the sample may have different thicknesses, in particular a thickness from several tens of micrometers (μm), notably from 10 to 20 μm.

This section comprising the sample 1 is positioned on a support 2, preferably the latter consist in a transparent slide to average infrared radiations of the electromagnetic spectrum. The section comprising the sample 1 is spread out on said support 2. No other additional preparation is required. As such, said sample 1 is not colored.

Except for this preparation operation, said system gives the possibility of automating the detection of tissue fibrosis on a sample 1 and the quantification of the tissue fibrosis as compared with other tissues of said sample 1, doing without any human intervention, thereby providing increased reproducibility and objective results.

To do this, the system according to the invention involves infrared acquisition of the sample 1, and then a specific computer processing of the pieces of spectral information from said acquisition.

As regards the infrared acquisition, it is carried out by sweeping points of said sample 1.

To do this, the support 2 is placed at receiving means 3 such as a motor-driven plate. The latter give the possibility of maintaining in place said support 2 during the acquisition operation.

This acquisition is achieved with acquisition means 4 by infrared spectroscopy positioned facing said receiving means 3.

Preferentially, the invention involves Fourier transform infrared spectroscopy. It associates polychromatic excitation with an infrared micro-spectrometer for detecting the average infra-red absorption by the sample 1. Subsidiarily, continuous cooling of the detector may be contemplated, in order to limit the measurement noise.

It will then be noted that said support 2 is adapted to infrared spectroscopy, in particular with a Fourier transform. In other words, the support 2 consists of a material without any parasitic infrared signal, this material is for example calcium fluoride or ZnSe for transmission acquisition. Glass slides metallized by silver deposition may also be used for acquisition in a reflection mode.

This acquisition is carried out by sweeping points of said sample 1. Such sweeping may stem from the displacement of the acquisition means 4 relatively to the receiving means 3. Preferentially, said receiving means 3 are the ones which are provided to be mobile, while the acquisition means 4 are fixed. In other words, this is relative sweeping of said support 2 by said infrared acquisition means 4. To do this, the invention integrates means 5 for controlling the displacements of said receiving means 3.

Further, these control means 5 also give the possibility of automatically handling the acquisition parameters of the means 4.

Thus, the control means 5 give the possibility of automating and of making self-contain the step for acquisition of the entireness of the sample 1.

During the acquisition step, each point produces an infrared spectrum. Consequently, the infrared spectrum produced by each acquired point is converted into at least one spectral image 6.

Said acquisition means 4 are the ones which convert the infrared spectrum produced by each acquired point into said spectral image 6.

As such, said spectral image is a digital representation of all the acquired points. The points are located by their coordinates in space according to two dimensions. Each point forms a pixel of said image 6.

In order to quantify fibrosis, a numerical processing operation is carried out on said spectral image 6. This processing is carried out by suitable processing means 8. The processing operation consists in a discrimination between at least physiological collagen and pathological collagen by assigning to each point a spectral class by comparison with a numerical model of spectra 7.

Such a model consists in the acquisition of a large so called "training" panel of renal biopsies with different degrees of fibrosis, for which the assignment of each class was achieved by an anatomopathologist expert in renal pathology, and then this panel underwent internal validation on a second panel of biopsies. A control of the results of the model was carried out and then external validation on a third panel of analyzed blind biopsies was carried out in order to reinforce the robustness of this model.

Thus, from the values of the spectra measured of the points of the sample, it is possible to differentiate the tissues having a fibrosis from the other tissues.

In particular, said classes may be at least two in number, but preferentially four: physiological collagen, collagen from the fibrosis, inflammation and "normal" parenchyma (non-collagen, non-fibrous and non-inflammatory). Other classes may optionally be added.

First, the processing comprises an automated pre-processing step of the spectra, consisting in removing the background noise from the support 2 and from the detector and in the neutralization of the spectral interferences of paraffin. This pre-processing therefore consist of improving the quality of the image 6, by also removing the spectra with insufficient signal-to-noise ratio. Said pre-processing is carried out automatically, with a dedicated algorithm.

Next, the points having a similar spectral class are quantified statistically and the result 10 is recorded. The processing means 8 are the ones which automatically ensure these statistically multi-varied groups per class. Digital recording means 9 then ensure the saving of the result 10 stemming from said processing means 8.

By "similarity" one refers to points having received as an assignment, an identical class or else equivalent classes. In the latter case, several classes may be grouped into a single and same global class, of larger size.

In particular, the points of a same class are statistically quantified as a surface percentage 11 of the total surface area of said sample 1. In other words, the percentage ratio of the number of points of each class relatively to the total number of points, corresponding to the total surface area of the sample 1 is calculated.

Thus, it is possible to automatically obtain the proportion of tissues having a pathological fibrosis relatively to the other healthy tissues. Consequently, it is no longer necessary to have a specialized operator interpret the results, which are directly available as a representative value of the progress of the fibrosis.

Subsidiarily, the invention provides improvement in the relevance of the result 10 from the automatic processing, by combining all the results within a data base. Consequently, the obtained result will be coupled with the results established earlier during the previous analysis of other samples. To do this, said result 10 is combined to said model 7 before repeating said method with another sample. This development possibility of the model in particular allows refinement of the spectral classes in order to include or exclude pixels in a given class and thereby even improve the robustness of the model.

As mentioned earlier, the object of the invention is a method for detecting and quantifying fibrosis, wherein at least:
- a fixed non-colored tissue sample 1 is positioned on a support 2;
- infrared acquisition is carried out by sweeping points of said sample 1;
- the infrared spectrum produced by each acquired point is converted into at least one spectral image 6;
- a digital processing operation of said spectral image 6 is carried out by discrimination from among at least physiological collagen and pathological collagen from the fibrosis by assigning to each point a spectral class by statistical comparison with a numerical model of spectra;
- the points are quantified having a similar spectral class and the result is recorded.

The invention also relates to a device for detecting and quantifying fibrosis, comprising at least:
- means 3 for receiving a support 2 of a tissue sample 1;
- means 4 for acquiring by Fourier transform infrared spectroscopy, positioned facing said receiving means 3, said acquisition means 4 converting the infrared spectrum produced by each acquired point into at least one spectral image 6;
- numerical processing means of said spectral image 6 by discrimination between at least physiological collagen and pathological collagen by assigning to each point a spectral class by statistical comparison with a numerical model of spectra with which said processing means are provided, said processing means quantifying the points having a similar spectral class;
- means for digital recording of the result of said processing means.

Subsidiarily, all the elements, aspects and digital and computer means, in particular the algorithms and the numerical models, are executed through dedicated digital and computer terminals, notably connected with each other via networks and suitable communication means.

We claim:

1. A method for detecting and quantifying fibrosis, the method comprising the steps of:
   positioning a fixed non-colored tissue sample on a support;
   performing an infrared acquisition by sweeping points of said sample;
   producing an infrared spectrum, wherein each acquired point is converted into at least one spectral image;
   digital processing of the spectral image is carried out by discrimination between at least physiological collagen and pathological collagen from fibrosis by assigning to each point a spectral class defined by an algorithm classifying the spectra according to spectral similarities;
   assigning a condition to each class by statistical comparison with a numerical model of spectra;
   quantifying a relative surface area occupied by the points of each condition; and
   recording a result.

2. The method, according to claim 1, wherein the step of performing said infrared acquisition is carried out by Fourier transform infrared spectroscopy.

3. The method, according to claim 1, wherein the step of digital processing comprises:
   performing a spectral removal of background noises from the support and from the detector and in the neutralization of the interferences of paraffin before discrimination between at least physiological collagen and pathological collagen.

4. The method, according to claim 1, wherein the step of digital processing comprises: assigning four spectral classes, wherein conditions correspond to: normal, fibrosis, non-fibrous collagen, and inflammation.

5. The method, according to claim 1, wherein the step of digital processing comprises: said discrimination being carried out by comparing value of the spectrum of each point with ranges of values of spectra of said model.

6. The method, according to claim 1, wherein the points of a same class are statistically quantified as a surface percentage of the total surface area of said sample in the step of digital processing.

7. The method, according to claim 1, wherein the step of recording comprises: combining said result with said model before repeating said method with another sample.

8. A device for detecting and quantifying fibrosis, said device comprising:
   means for receiving a support of a tissue sample;
   means for acquisition by Fourier transform infrared spectroscopy, positioned facing said receiving means, said means for acquisition converting the infrared spectrum produced by each acquired point into at least one spectral image;
   means for digital processing of said spectral image by discrimination between at least physiological collagen and pathological collagen by assigning to each point a spectral class by statistical comparison with a numerical model of spectra with which said processing means are provided, said processing means quantifying the points having a similar spectral class; and
   means for digitally recording the result of said processing means.

9. The device, according to claim 8, wherein said receiving means are motor-driven, said device further comprising: means for controlling the displacements of said receiving means, so as to carry out a relative sweep of said support by said infrared acquisition means.

* * * * *